United States Patent
Shirota

(10) Patent No.: US 11,116,472 B2
(45) Date of Patent: Sep. 14, 2021

(54) X-RAY IMAGE CAPTURING APPARATUS AND X-RAY IMAGE CAPTURING METHOD

(71) Applicant: Shimadzu Corporation, Kyoto (JP)

(72) Inventor: Ken Shirota, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 225 days.

(21) Appl. No.: 16/413,514

(22) Filed: May 15, 2019

(65) Prior Publication Data
US 2019/0380674 A1    Dec. 19, 2019

(30) Foreign Application Priority Data
Jun. 14, 2018    (JP) .............................. JP2018-113805

(51) Int. Cl.
  *A61B 6/00*    (2006.01)
  *A61B 6/03*    (2006.01)
  *A61B 6/02*    (2006.01)

(52) U.S. Cl.
  CPC .............. *A61B 6/584* (2013.01); *A61B 6/025* (2013.01); *A61B 6/032* (2013.01); *A61B 6/4452* (2013.01); *A61B 6/461* (2013.01); *A61B 6/467* (2013.01); *A61B 6/547* (2013.01); *A61B 6/548* (2013.01); *A61B 6/588* (2013.01)

(58) Field of Classification Search
  CPC ......... A61B 6/025; A61B 6/583; A61B 6/584; G01N 23/044
  See application file for complete search history.

(56) References Cited

U.S. PATENT DOCUMENTS

| | | | | |
|---|---|---|---|---|
| 5,572,567 A * | 11/1996 | Khutoryansky | ..... | A61B 6/4283 378/177 |
| 6,196,715 B1 * | 3/2001 | Nambu | ..... | A61B 6/00 378/11 |
| 7,874,729 B2 | 1/2011 | Okuno et al. | | |
| 2004/0264648 A1 * | 12/2004 | Claus | ..... | A61B 6/583 378/163 |
| 2008/0108895 A1 * | 5/2008 | Sabol | ..... | G01N 23/044 378/26 |
| 2016/0120495 A1 * | 5/2016 | Miyazawa | ..... | A61B 6/025 378/21 |

FOREIGN PATENT DOCUMENTS

JP    2008-125981 A    6/2008

OTHER PUBLICATIONS

Press Release by Shimadzu Corporation: "Development of a new technology to obtain tomosynthesis images regardless of X-ray equipment" Oct. 11, 2017. Available on: https://www.shimadzu.co.jp/news/press/n00kbc000000dzil.html, submitted with a machine translation.

Kawano et al. "Development of Auto Positioning System for X-ray General Radiography" Shimadzu Review vol. 63 [ 3 • 4] (2006). Available at: (https://www.shimadzu.co.jp/products/tec_news/srv63_34/report05.html), submitted with a machine translation.

* cited by examiner

Primary Examiner — Chih-Cheng Kao
(74) Attorney, Agent, or Firm — Muir Patent Law, PLLC

(57) ABSTRACT

An X-ray image capturing apparatus includes a target determiner that determines a target position of an imager and a target angle of the imager based on imaging content information for generating a tomographic image, and a drive controller that controls a drive to be driven such that a relative position of the imager corresponds to the target position and a relative angle of the imager corresponds to the target angle.

10 Claims, 7 Drawing Sheets

FIG.8
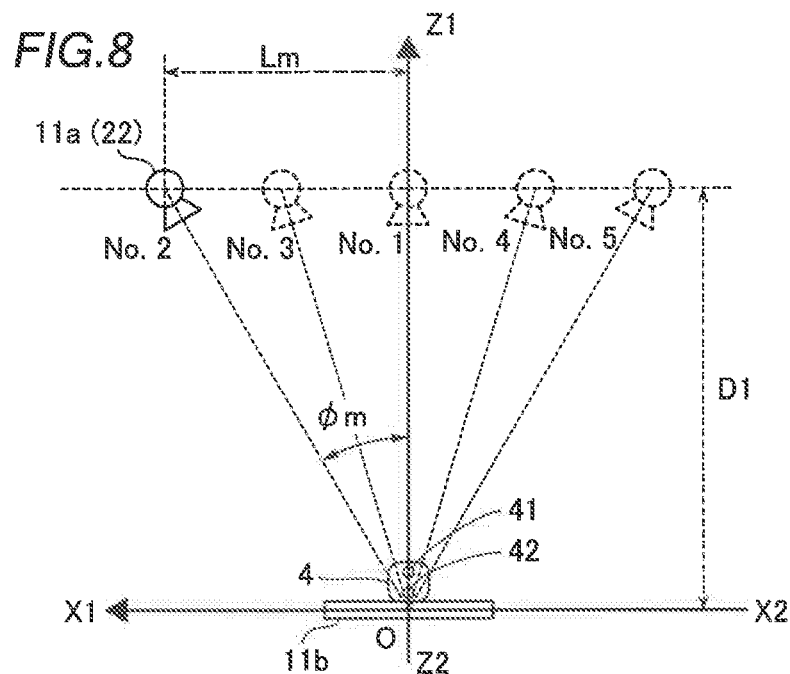
FIG.9
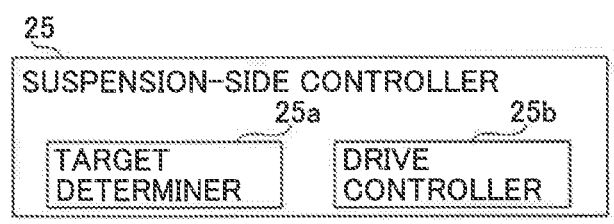
FIG.10
| n | 2 | 3 | 4 | 5 | 6 | 7 |
|---|---|---|---|---|---|---|
| N = 3 | Lm | −Lm | | | | |
| N = 5 | Lm | Lm/2 | −Lm/2 | −Lm | | |
| N = 7 | Lm | 2Lm/3 | Lm/3 | −Lm/3 | −2Lm/3 | −Lm |

X-RAY IMAGE CAPTURING APPARATUS AND X-RAY IMAGE CAPTURING METHOD

CROSS-REFERENCE TO RELATED APPLICATIONS

This application claims the benefit of priority to Japanese Patent Application No. 2018-113805 filed on Jun. 14, 2018. The entire contents of this application are hereby incorporated herein by reference.

BACKGROUND OF THE INVENTION

Field of the Invention

The present invention relates to an X-ray image capturing apparatus and an X-ray image capturing method, and more particularly, it relates to an X-ray image capturing apparatus and an X-ray image capturing method, each of which generates a tomographic image based on a plurality of X-ray images.

Description of the Background Art

An X-ray image capturing apparatus and an X-ray image capturing method, each of which generates a tomographic image based on a plurality of X-ray images are known in general, as disclosed in "Development of New Technology to Obtain Tomosynthesis Image Regardless of X-ray Imaging Apparatus", [online], Shimadzu Corporation, [searched on May 16, 2018], Internet <URL: https://www.shimadzu.co.jp/news/press/n00kbc000000dzil.html> (hereinafter referred to as the "Non-Patent Document 1"), for example.

The aforementioned Non-Patent Document 1 discloses an X-ray image capturing apparatus that generates a tomographic image based on a plurality of X-ray images captured by X-ray imaging. In this X-ray image capturing apparatus, X-ray imaging is performed while the arrangement position of an X-ray tube and the X-ray irradiation angle are changed by an operator in a state in which a positioning phantom is disposed in the vicinity of an imaging area (region of interest) of a subject. Then, the X-ray image capturing apparatus generates a tomographic image (tomosynthesis image) based on the reference position information of the positioning phantom that appears in each X-ray image, using a plurality of X-ray images captured by X-ray imaging. Thus, even when the X-ray image capturing apparatus is a general X-ray imaging apparatus (even when a precise machine control mechanism is not mounted as compared with a dedicated tomosynthesis imaging apparatus), this X-ray image capturing apparatus acquires a tomosynthesis image having a spatial resolution equivalent to that of a dedicated tomosynthesis imaging apparatus.

In addition, an X-ray image capturing apparatus including a moving means and a rotating means that move an X-ray tube is known in general, as disclosed in Japanese Patent Laid-Open No. 2008-125981, for example.

The aforementioned Japanese Patent Laid-Open No. 2008-125981 discloses a general imaging system including an X-ray emitting means parallel movement holding means (hereinafter referred to as the "moving means") and an X-ray emitting means rotation holding means (hereinafter referred to as the "rotating means") that move an X-ray tube. This general imaging system includes a controlling means, a selecting means, a storing means, the X-ray tube, a flat panel detector (hereinafter referred to as the "FPD"), and a driving means. In this general imaging system, a method/target area to be imaged, etc., are selected by the selecting means to read out an imaging condition stored in advance as an anatomical program in the storing means. Then, the controlling means activates the driving means built in the moving means and the rotating means to move and rotate the X-ray tube such that the positional relationship between the X-ray tube and the FPD stored corresponding to the anatomical program is made. Thus, in this general imaging system, the X-ray tube can be automatically positioned.

Here, in an X-ray image capturing apparatus that generates a tomographic image (tomosynthesis image) based on the reference position information of the positioning phantom disclosed in the aforementioned Non-Patent Document 1, in order to reduce the work burden on the operator, the structure capable of automatically positioning the X-ray tube in the general imaging system disclosed in Japanese Patent Laid-Open No. 2008-125981 is conceivably applied. However, in this X-ray image capturing apparatus, it is necessary to store (register) a plurality of imaging conditions (information about the arrangement position of the X-ray tube and information about the X-ray irradiation angle) for generating a tomosynthesis image of one area to be imaged in the storing means in advance. Depending on the area to be imaged, the appropriate arrangement position of the X-ray tube, the X-ray irradiation angle, and the number of images to be captured are different, and thus a registration operation for registering the imaging conditions in the storing means becomes complicated. Furthermore, in order to generate a tomosynthesis image, the number of imaging conditions that needs to be stored in the storing means increases, and thus it is necessary to increase the size of the storing means (increase the capacity). Therefore, in general, an X-ray image capturing apparatus (and an X-ray image capturing method) capable of significantly reducing or preventing an increase in the number of imaging conditions (imaging content information) that needs to be stored in advance while reducing the work burden on an operator even when generating a tomosynthesis image (a tomographic image parallel to the movement direction of an imager) based on the reference position information has been desired.

SUMMARY OF THE INVENTION

The present invention has been proposed in order to solve the aforementioned problems, and an object of the present invention is to provide an X-ray image capturing apparatus and an X-ray image capturing method each capable of significantly reducing or preventing an increase in the number of pieces of imaging content information that needs to be stored in advance while reducing the work burden on an operator even when generating a tomographic image parallel to the movement direction of an imager based on reference position information.

In order to attain the aforementioned object, an X-ray image capturing apparatus according to a first aspect of the present invention includes an imager including an X-ray source and a detector that detects X-rays, a movement unit including a position change mechanism that changes a relative position and a relative angle between the X-ray source and the detector and a drive that drives the position change mechanism, and that moves the imager, an image generator that generates a tomographic image parallel to a movement direction of the imager based on a plurality of X-ray images captured by X-ray imaging by the imager and reference position information, which is position information of a position reference portion that appears in the plurality of X-ray images, a target determiner that determines a target position of the imager and a target angle of the imager based on imaging content information for generating the tomographic image in order to capture each of the X-ray images, and a drive controller that controls the drive to be driven such that a relative position of the imager corresponds to the target position of the imager and a relative angle of the imager corresponds to the target angle of the imager.

As described above, the X-ray image capturing apparatus according to the first aspect of the present invention includes the target determiner that determines the target position of the imager and the target angle of the imager based on the imaging content information for generating the tomographic image in order to capture each of the X-ray images, and the drive controller that controls the drive to be driven such that the relative position of the imager corresponds to the target position of the imager and the relative angle of the imager corresponds to the target angle of the imager. Accordingly, a plurality of target positions and a plurality of target angles can be determined (calculated, for example) based on the imaging content information. Consequently, there is no need to prepare (register and store) the imaging content information for each X-ray image, and thus an increase in the number of pieces of imaging content information can be significantly reduced or prevented. In addition, the drive controller can automatically drive the drive (move the imager) such that the relative position of the imager corresponds to the target position of the imager and the relative angle of the imager corresponds to the target angle of the imager, and thus the work burden on an operator can be reduced as compared with the case in which the imager is manually moved by the operator. Consequently, even when the tomographic image parallel to the movement direction of the imager is generated based on the reference position information, an increase in the number of pieces of imaging content information that needs to be stored in advance can be significantly reduced or prevented while the work burden on the operator is reduced.

In the aforementioned X-ray image capturing apparatus according to the first aspect, the imaging content information preferably includes angle information of the imager and number information of the X-ray images to be captured by X-ray imaging, and the target determiner preferably determines the target position of the imager and the target angle of the imager corresponding to each of the plurality of X-ray images to be captured based on the angle information of the imager and the number information of the X-ray images. According to this structure, the target determiner can acquire the number of X-ray images required to generate (reconstruct) a tomosynthesis image and the angle information of the imager when the X-ray images are captured by X-ray imaging, and thus the target position and the target angle corresponding to each X-ray image required to generate (reconstruct) the tomosynthesis image can be determined (calculated) based on one piece of imaging content information.

The aforementioned X-ray image capturing apparatus according to the first aspect preferably further includes an X-ray generation unit including an X-ray source controller that controls operation of the X-ray source, the movement unit preferably includes a movement unit-side controller including the target determiner, and the movement unit-side controller preferably acquires the imaging content information from the X-ray source controller of the X-ray generation unit. According to this structure, even when the imaging content information is stored (or set) in the X-ray generation unit different from the movement unit, the movement unit-side controller including the target determiner can acquire the imaging content information from the X-ray generation unit.

In this case, the imaging content information is preferably comment information input via an input operation by an operator, and the movement unit-side controller preferably acquires the comment information from the X-ray source controller. Here, in a general X-ray image capturing apparatus, an X-ray source controller of an X-ray generation unit can transmit comment information input via an input operation by an operator to a movement unit-side controller. In view of this, in the present invention, the movement unit-side controller can acquire the imaging content information as the comment information from the X-ray source controller, and thus the operator inputs the imaging content information into the comment information without using a dedicated X-ray source controller (without changing software of the X-ray source controller in order to apply the present invention) such that the target determiner of the movement unit can acquire the imaging content information.

In the aforementioned X-ray image capturing apparatus in which the movement unit-side controller acquires the comment information from the X-ray source controller, the X-ray generation unit preferably includes a comment input operation unit that receives the input operation for the comment information from the operator and a display that displays the comment information. According to this structure, the input operation by the operator can be received through the comment input operation unit while the operator visually recognizes the contents of the comment information on the display, and thus the convenience of the input operation by the operator can be improved.

In the aforementioned X-ray image capturing apparatus in which the movement unit-side controller acquires the imaging content information from the X-ray source controller, the imaging content information preferably contains imaging step information indicating which one of the plurality of X-ray images an X-ray image to be next captured by X-ray imaging corresponds to, and the drive controller preferably acquires the imaging step information from the X-ray source controller, and controls the drive to be driven such that the relative position of the imager corresponds to the target position of the imager corresponding to the acquired imaging step information and the relative angle of the imager corresponds to the target angle of the imager corresponding to the acquired imaging step information. According to this structure, even when the plurality of target positions and the plurality of target angles are determined (calculated), the imager can be appropriately moved and changed in angle to the target position and the target angle corresponding to the X-ray image to be next captured by X-ray imaging based on the imaging step information.

In the aforementioned X-ray image capturing apparatus including the X-ray generation unit, the X-ray generation unit preferably includes a drive start operation unit that receives an input operation indicating that driving of the drive is to be started from an operator, and the drive controller preferably starts the driving of the drive such that the relative position of the imager corresponds to the target position of the imager and the relative angle of the imager corresponds to the target angle of the imager in accordance with the input operation indicating that the driving of the drive is to be started. According to this structure, the operator can start driving of the drive through the drive start operation unit at the intended time (timing). Consequently, when the X-ray image capturing apparatus is used as a medical X-ray image capturing apparatus, the drive can be driven (the imager can be moved) at the appropriate timing according to the state (such as the posture) of a subject.

In the aforementioned X-ray image capturing apparatus according to the first aspect, the target determiner preferably acquires imager distance information, which is information indicating a distance from the detector to the X-ray source when a first X-ray image is captured by X-ray imaging, and dimension information, which is information indicating a dimension of a region of the detector irradiated with the X-rays from the X-ray source, and determines the target position of the imager and the target angle of the imager based on the imager distance information, the dimension information, and the imaging content information. According to this structure, the target position of the imager and the target angle of the imager can be easily determined (calculated) from the imager distance information (SID: source image receptor distance, for example) and the dimension information (irradiation field size).

In this case, the image generator preferably generates the tomographic image based on the plurality of X-ray images including the first X-ray image and the reference position information. According to this structure, the first X-ray image captured by X-ray imaging to acquire the imager distance information and the dimension information can also be used to generate (reconstruct) the tomographic image (tomosynthesis image), and thus an increase in the number of times of X-ray imaging can be significantly reduced or prevented. Consequently, an increase in the X-ray irradiation dose and an increase in the number of operation steps related to X-ray imaging can be significantly reduced or prevented.

The aforementioned X-ray image capturing apparatus according to the first aspect preferably further includes a phantom including the position reference portion and disposed at a position at which the position reference portion appears together with a region of interest of a subject in the plurality of X-ray images, the movement unit preferably changes the relative position between the X-ray source and the detector and the relative angle between the X-ray source and the detector in a state in which a relative position and a relative angle between the detector and the phantom are kept constant, and the target determiner preferably determines an X-ray source target position of the X-ray source with respect to the detector as the target position of the imager and an X-ray source target angle of the X-ray source with respect to the detector as the target angle of the imager based on the imaging content information. According to this structure, changes (shifts) in the relative position and the relative angle between the detector and the phantom can be significantly reduced or prevented, and thus a more accurate tomographic image (tomosynthesis image) can be generated. Furthermore, it is not necessary to determine the target position and the target angle of the detector by determining the X-ray source target position and the X-ray source target angle, and thus an increase in the control load on determination processing (calculation processing) performed by the target determiner can be significantly reduced or prevented.

An X-ray image capturing method according to a second aspect of the present invention is an X-ray image capturing method for generating a tomographic image parallel to a movement direction of an imager, which is a direction in which the imager is moved by a movement unit, based on a plurality of X-ray images captured by X-ray imaging by the imager and reference position information, which is position information of a position reference portion that appears in the plurality of X-ray images. In the method, a target position of the imager and a target angle of the imager are determined based on imaging content information for generating the tomographic image in order to capture each of the X-ray images, and thereafter, the movement unit causes a relative position of the imager to correspond to the target position of the imager and causes a relative angle of the imager to correspond to the target angle of the imager.

In the X-ray image capturing method according to the second aspect of the present invention, due to the configuration described above, it is possible to significantly reduce or prevent an increase in the number of pieces of imaging content information that needs to be stored in advance while the work burden on an operator is reduced even when the tomographic image parallel to the movement direction of the imager is generated based on the reference position information.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 8 is a diagram illustrating movement of an imager according to the embodiment.

FIG. 9 is a block diagram showing the structure of a suspension-side controller according to the embodiment.

FIG. 10 is a diagram illustrating determination of the target offset distance according to the embodiment.

DESCRIPTION OF THE PREFERRED EMBODIMENTS

Figure 1:
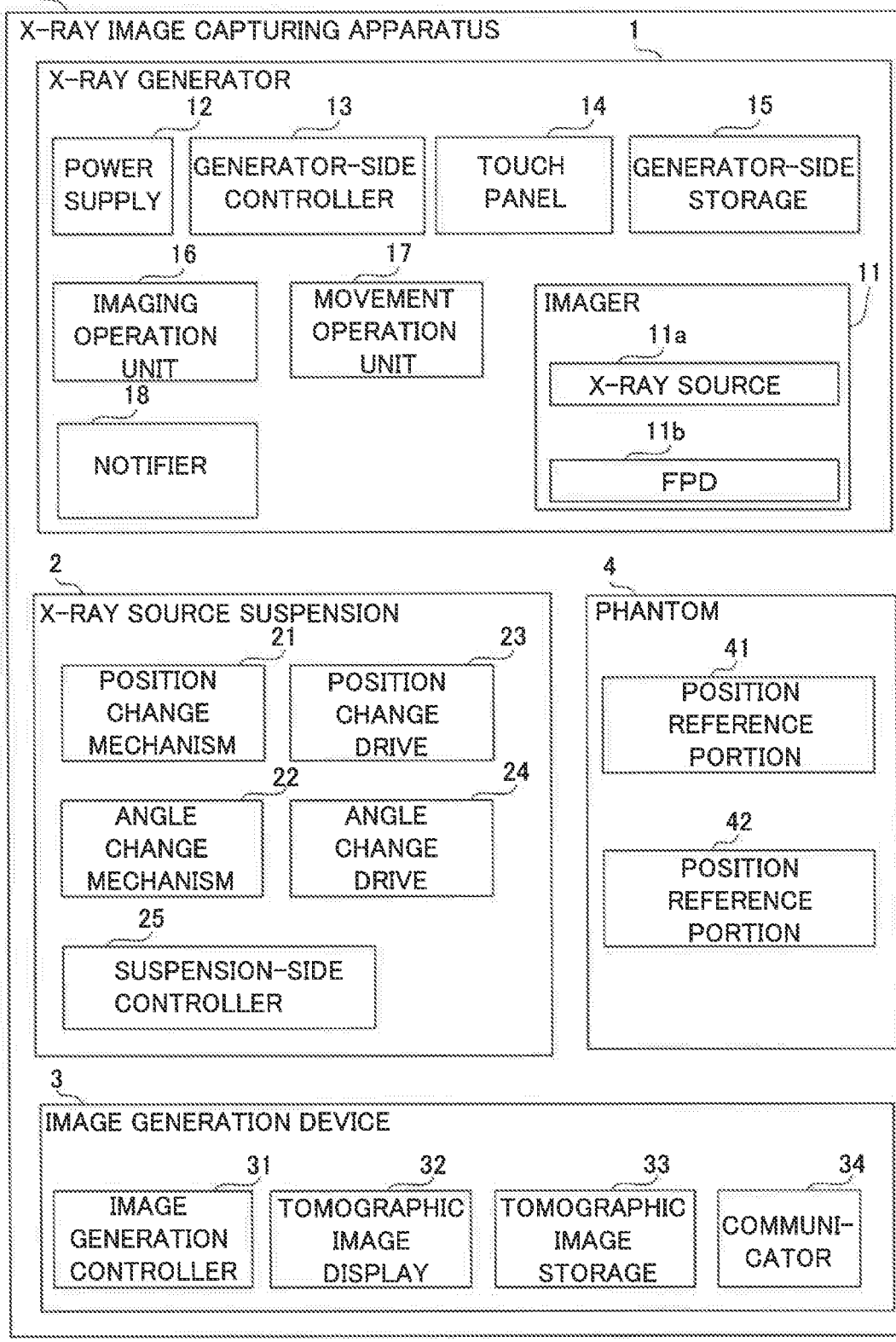
FIG. 1 is a block diagram showing the overall structure of an X-ray image capturing apparatus according to an embodiment.

An embodiment of the present invention is hereinafter described with reference to the drawings.

The structure of an X-ray image capturing apparatus 100 according to an embodiment of the present invention is now described with reference to FIGS. 1 to 10.

The X-ray image capturing apparatus 100 is an image apparatus that generates a tomosynthesis image on a general X-ray imaging apparatus or X-ray television system using a universal tomosynthesis technique. Here, the universal tomosynthesis technique is a technique to generate a tomographic image Et (tomosynthesis image) parallel to the moving direction of an imager 11 based on reference position information F, which is the position information of position reference portions 41 and 42 (phantom 4) that appear in a plurality of X-ray images E. That is, the X-ray image capturing apparatus 100 reconstruct the plurality of X-ray images E to generate a tomographic image Et. In addition, the X-ray image capturing apparatus 100 is a medical X-ray image capturing apparatus using a human body or an animal as a subject T.

The X-ray image capturing apparatus 100 has an auto positioning function. That is, in the X-ray image capturing apparatus 100, the movement and angle change of the imager 11 are automated (motorized). Furthermore, in the X-ray image capturing apparatus 100, the movement and angle of the imager 11 can be changed in any of a state in which the subject T is lying down (see FIG. 2) and a state in which the subject T is standing (not shown). In the following description, only the case in which the lying-down subject T is imaged is described, and description of the case in which the standing subject T is imaged is omitted.

In the present specification, in order to construct a tomosynthesis image, a direction in which the imager 11 is moved (a direction in which an X-ray source 11a described below linearly moves) is defined as an X direction. In an example shown in FIG. 2, the X direction is a direction in which the head and the leg of the subject T are connected. Furthermore, a direction orthogonal to the movement direction of the imager 11 and in which the X-ray source 11a faces a flat panel detector 11b (hereinafter referred to as the "FPD 11b") described below is defined as a Z direction. Furthermore, a direction orthogonal to the X direction and orthogonal to the Z direction is defined as a Y direction.

As shown in FIG. 1, the X-ray image capturing apparatus 100 includes an X-ray generator 1 (hereinafter referred to as the "generator 1"), an X-ray source suspension 2 (hereinafter referred to as the "suspension 2"), an image generation device 3, and the phantom 4. The generator 1 is an example of an "X-ray generation unit" in the claims. The suspension 2 is an example of a "movement unit" in the claims. The image generation device 3 is an example of an "image generator" in the claims.

(Structure of X-ray Generator)

The generator 1 is a so-called X-ray high voltage device. As shown in FIG. 1, the generator 1 includes the imager 11, a power supply 12, a generator-side controller 13, a touch panel 14, a generator-side storage 15, a imaging operation unit 16, a movement operation unit 17, and a notifier 18. The generator-side controller 13 is an example of an "X-ray source controller" in the claims. The touch panel 14 is an example of a "display" and a "comment input operation unit" in the claims. The movement operation unit 17 is an example of a "drive start operation unit" in the claims.

The imager 11 includes the X-ray source 11a and the FPD 11b that detects X-rays. The X-ray source 11a radiates X-rays toward the FPD 11b. For example, the X-ray source 11a includes an X-ray tube, a collimator, etc. In addition, the FPD 11b detects X-rays radiated by the X-ray source 11a and transmitted through a region of interest ROI of the subject T or the phantom 4. The FPD 11b transmits a detection signal to the image generation device 3. For example, the FPD 11b includes a plurality of conversion elements, a plurality of pixel electrodes, etc.

The power supply 12 converts commercial power supplied from the outside into electric power having a voltage value and a current value based on a command (imaging program) from the generator-side controller 13, and supplies (applies) the converted electric power to the X-ray source 11a during a period based on the imaging program. In other words, the power supply 12 functions as a driver of the X-ray source 11a.

The generator-side controller 13 includes a processor such as a CPU (Central Processing Unit) and an FPGA (Field-Programmable Gate Array). The generator-side controller 13 controls the overall operation of the generator 1 by executing control programs stored in the generator-side storage 15.

The touch panel 14 can display an image, and receives an input operation (a touch operation on a display surface) from an operator. For example, the touch panel 14 switchably displays an imaging step display screen P1 (see FIG. 3), a comment input operation screen P3 (see FIG. 5), and an imaging program display screen P2 (see FIG. 6).

The generator-side storage 15 is a nonvolatile memory capable of storing the control programs, imaging programs, etc. For example, the generator-side storage 15 includes an EPROM (Erasable Programmable Read Only Memory).

Each of the imaging operation unit 16 and the movement operation unit 17 is a hand switch, a push button, or a foot switch, for example, and receives an input operation from the operator. The imaging operation unit 16 receives an input operation to instruct the imager 11 to perform X-ray imaging, and transmits this input operation to the generator-side controller 13. The movement operation unit 17 receives an input operation indicating that driving of a position change drive 23 and an angle change drive 24 is to be started from the operator. For example, the movement operation unit 17 transmits the received input operation as a drive start signal S1 to a suspension-side controller 25.

The notifier 18 is an indicator lamp (lamp) or a sound output, for example. For example, the notifier 18 turns on the indicator lamp or emits a sound from the sound output based on a command from the generator-side controller 13 when the movement and angle change of the imager 11 are completed (when a movement completion signal S2 is acquired). In addition, the notifier 18 turns on the indicator lamp or emits a sound from the sound output based on a command from the generator-side controller 13 during X-ray imaging or when X-ray imaging is completed.

<Structure Related to Control of X-Ray Generator>

The generator-side controller 13 can perform wired communication or wireless communication with the suspension-side controller 25 of the suspension 2. In the present embodiment, the generator-side controller 13 transmits (sends) imaging content information G to the suspension-side controller 25 of the suspension 2. Control of the generator 1 described below is executed by the generator-side controller 13.

Figure 3:
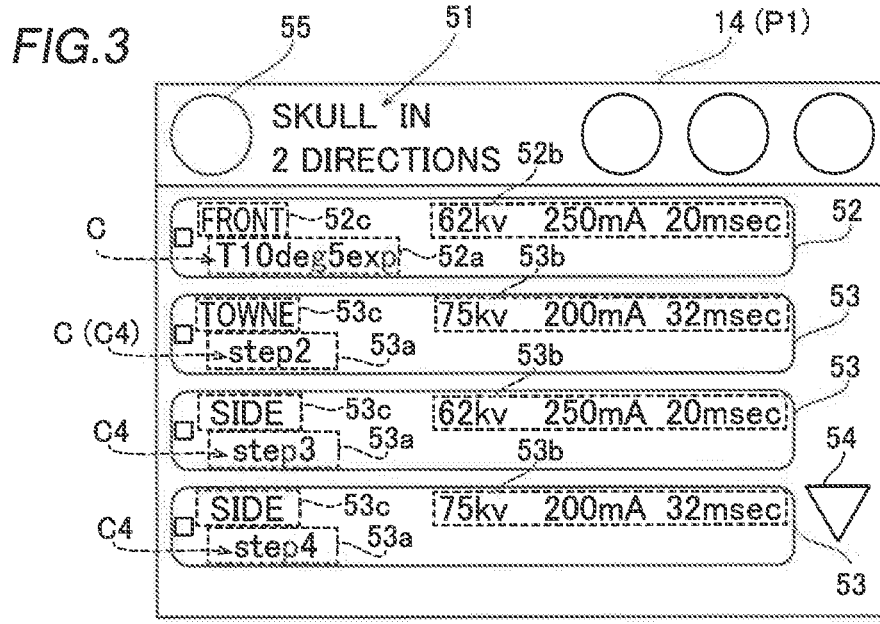
FIG. 3 is a diagram showing an imaging step display screen according to the embodiment.
Figure 4:
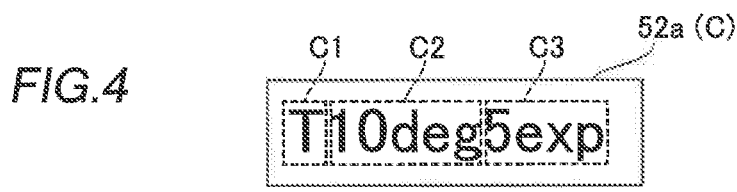
FIG. 4 is a diagram showing a first comment information display according to the embodiment.

The imaging content information G indicates the contents of imaging conditions under which the operator plan to perform X-ray imaging next, and is data that can be registered (stored) in the generator-side storage 15 by the operator. As shown in FIGS. 3 and 4, in the present embodiment, an input operation for comment information C is received from the operator, and the comment information C is displayed.

Specifically, as shown in FIG. 3, the imaging step display screen P1 is displayed on the touch panel 14. The imaging step display screen P1 includes an imaging program name display 51, a first imaging condition display 52 showing the imaging conditions corresponding to imaging of the first X-ray image E, second imaging condition displays 53 showing the imaging conditions corresponding to imaging of the second and subsequent X-ray images E, a step switching display 54 to switch the display contents of the first imaging condition display 52 and the second imaging condition displays 53, and a screen switching display 55 to switch the imaging step display screen P1 to the imaging program display screen P2.

On the imaging program name display 51, a name corresponding to an imaging program selected on the imaging program display screen P2 (see FIG. 6) described below is displayed. For example, the imaging program name display 51 includes the name of an area of the subject T to be imaged, an imaging direction with respect to the area, etc. Here, the imaging programs are information of a group of imaging conditions under which the plurality of X-ray images E required to generate (reconstruct) a tomosynthesis image are captured.

The first imaging condition display 52 shows imaging conditions under which a first captured X-ray image E1 (first image) among the plurality of X-ray images E (imaging programs) is captured. In the present embodiment, the first imaging condition display 52 includes a first comment information display 52a, a first X-ray source drive condition display 52b, and a first name display 52c.

As shown in FIG. 4, on the first comment information display 52a, the comment information C input via an input operation by the operator about imaging of the X-ray image E1 is displayed. The generator-side controller 13 transmits (sends) the imaging content information G including this comment information C to the suspension-side controller 25 of the suspension 2.

Figure 6:
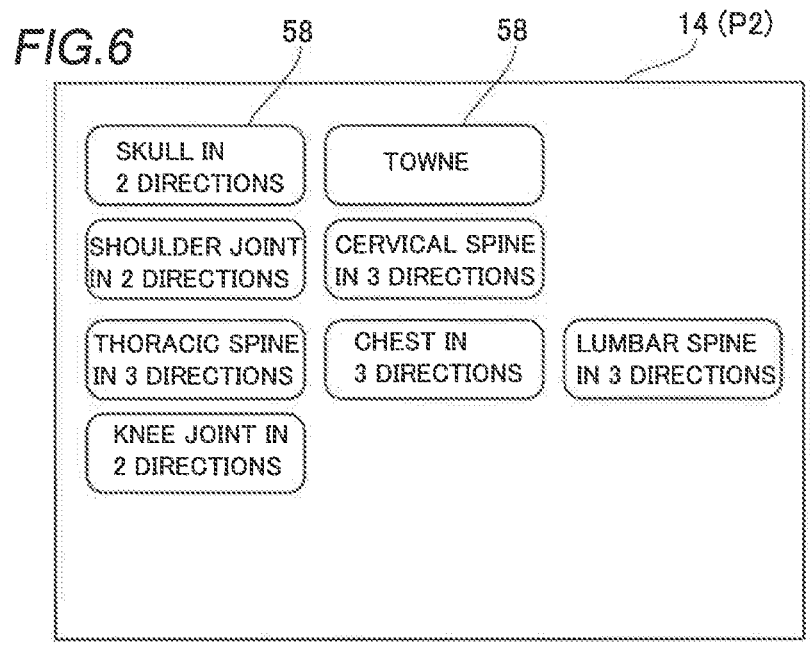
FIG. 6 is a diagram showing an imaging program display screen according to the embodiment.

Specifically, as shown in FIG. 6, in the present embodiment, the comment information C corresponding to the first comment information display 52a includes tomosynthesis command information C1 indicating that tomosynthesis imaging is performed instead of general imaging, the angle information C2 of the imager 11, and number information C3 (information about the total number N of images to be captured) of the X-ray images E to be captured by X-ray imaging. The tomosynthesis command information C1 is displayed on the touch panel 14 as "T", for example. Furthermore, when the maximum angle is 10 degrees, the angle information C2 is displayed on the touch panel 14 as "10 deg", for example. When the total number N of X-ray images E to be captured is five, the number information C3 is displayed on the touch panel 14 as "5 exp", for example.

As shown in FIG. 3, the first X-ray source drive condition display 52b includes displays of the value of a voltage applied to the X-ray source 11a, the value of a current that flows through the X-ray source 11a, the X-ray irradiation time, etc. when the X-ray image E1 is captured. In addition, the first name display 52c includes a display indicating a name for enabling the X-ray image E1 to be distinguished from another X-ray image E.

Figure 5:
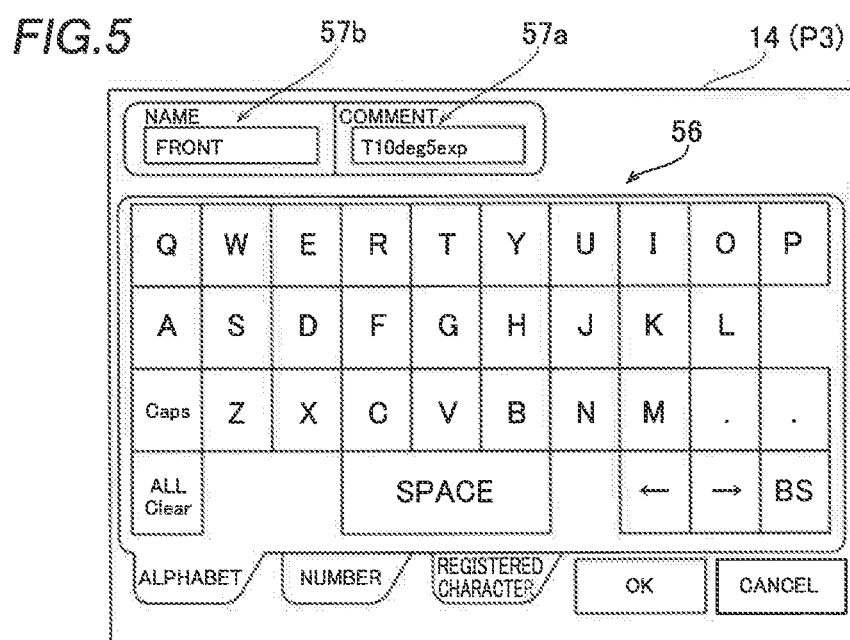
FIG. 5 is a diagram showing a comment input operation screen according to the embodiment.

As shown in FIG. 5, the contents of the first comment information display 52a and the first name display 52c can be set and changed (edited) by the operator. For example, when any one of the first comment information display 52a and the first X-ray source drive condition display 52b is touched, a display on the touch panel 14 is switched from the imaging step display screen P1 (see FIG. 3) to the comment input operation screen P3. The contents of the first X-ray source drive condition display 52b can be set and changed (edited) by the operator, similarly to the contents of the first comment information display 52a and the first name display 52c.

The comment input operation screen P3 includes a keyboard input operation display 56, an input comment column display 57a, and an input name column display 57b. On the keyboard input operation display 56, a character input is received based on a position (coordinates) touched by the operator. On the input comment column display 57a, comment information input by the operator through the keyboard input operation display 56 is displayed. Furthermore, on the input name column display 57b, a name input by the operator through the keyboard input operation display 56 is displayed.

As shown in FIG. 3, the second imaging condition displays 53 show imaging conditions under which second and subsequently captured X-ray images among the plurality of X-ray images E (imaging programs) are captured. In the present embodiment, the second imaging condition displays 53 each include a comment information display 53a, an X-ray source drive condition display 53b, and a name display 53c. The X-ray source drive condition display 53b and the name display 53c are configured similarly to the first X-ray source drive condition display 52b and the first name display 52c, and thus description thereof is omitted.

On the comment information display 53a, the comment information C input via the input operation by the operator about imaging of a predetermined X-ray image E of the second and subsequent X-ray images E is displayed. In the present embodiment, the comment information C displayed as the comment information display 53a is imaging step information C4 (information indicating "n") indicating which one of the plurality of X-ray images E the X-ray image E to be next captured by X-ray imaging corresponds to. When the X-ray image E to be captured next is an image to be captured second (second image), for example, the imaging step information C4 is displayed as "step 2", for example, on the comment information display 53a. In the following description, the X-ray image E to be next captured by X-ray imaging is described as an n-th (n is a natural number of 2 or more) X-ray image E. The comment information display 53a, the X-ray source drive condition display 53b, and the name display 53c can be set and changed on the comment input operation screen P3, similarly to the first comment information display 52a.

As shown in FIG. 6, on the touch panel 14, the imaging program display screen P2, on which one imaging program is selected from among a plurality of imaging programs, is displayed. On the imaging program display screen P2, selection displays 58, on which a plurality of imaging program names are displayed, are displayed in parallel in a matrix. The imaging step display screen P1 corresponding to a selection display 58 touched by the operator among the plurality of selection displays 58 is displayed on the touch panel 14. FIG. 5 shows an example in the case in which a selection display 58 showing "skull in 2 directions" on the imaging program display screen P2 is selected, for example.

(Structure of X-Ray Source Suspension)

Figure 2:
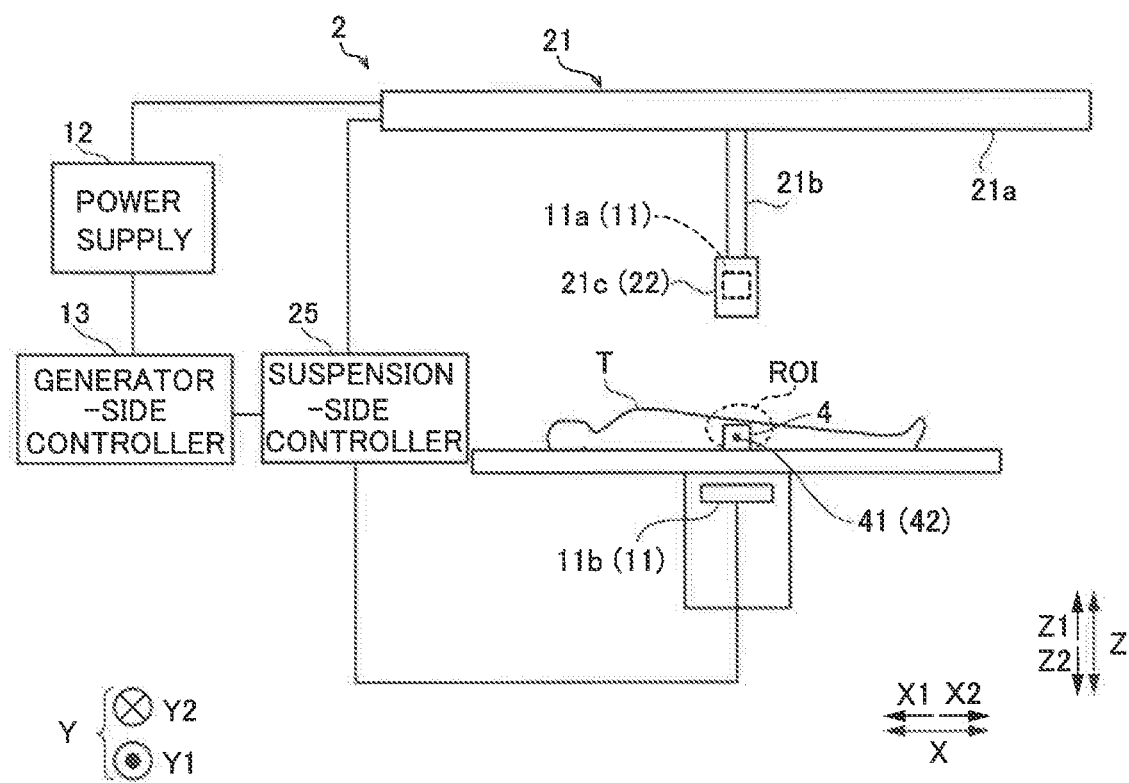
FIG. 2 is a diagram schematically showing the X-ray image capturing apparatus according to the embodiment.

As shown in FIG. 2, the suspension 2 includes a position change mechanism 21 that changes a relative position between the X-ray source 11a and the FPD 11b, and an angle change mechanism 22 that changes a relative angle between the X-ray source 11a and the FPD 11b. As shown in FIG. 1, the suspension 2 includes the position change drive 23 that drives the position change mechanism 21 and the angle change drive 24 that drives the angle change mechanism 22, and moves the imager 11. The suspension 2 further includes the suspension-side controller 25 including a target determiner 25a (see FIG. 9). The angle change mechanism 22 is an example of a "position change mechanism" in the claims. The position change drive 23 and the angle change drive 24 are examples of a "drive" in the claims. The suspension-side controller 25 is an example of a "movement unit-side controller" in the claims.

As shown in FIG. 2, the suspension 2 is an overhead traveling X-ray tube suspension, for example. That is, the position change mechanism 21 includes a linear movement mechanism 21a, a support rod 21b, and an X-ray source holder 21c. The linear movement mechanism 21a is a rail that enables the support rod 21b to slide in a direction parallel to the X direction and enables the support rod 21b to slide in a direction parallel to the Y direction, for example. Furthermore, the linear movement mechanism 21a is disposed on the ceiling of an examination room.

The support rod 21b extends in a Z2 direction from the linear movement mechanism 21a. In addition, the support rod 21b is expandable and contractible in the Z direction, and can change its height (its position in the Z direction). The X-ray source holder 21c is disposed in the vicinity of the tip of the support rod 21b on the Z2 direction side. The X-ray source holder 21c rotatably holds the X-ray source 11a. Further, the position change drive 23 is disposed (built) in either the position change mechanism 21 or the angle change mechanism 22, and the angle changing drive unit 24 is disposed (built) in either the position change mechanism 21 or the angle change mechanism 22.

Figure 7:
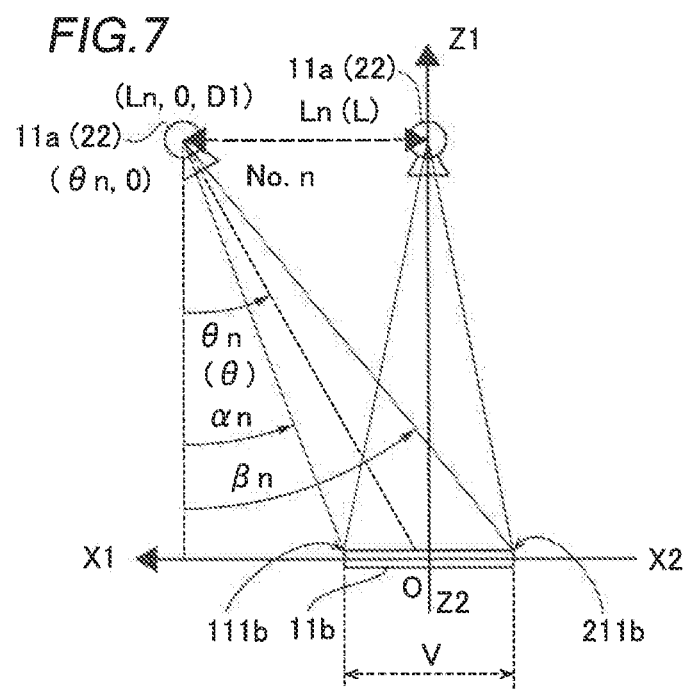
FIG. 7 is a diagram illustrating a target offset distance and a target offset angle according to the embodiment.

Specifically, as shown in FIG. 7, when a direction (Z direction) along a vertical direction is set to 0 degrees as a reference angle, the angle change mechanism 22 can change the X-ray irradiation center angle ($\theta n$, $\eta$) of the X-ray source 11a, which is the inclination angle of the X-ray source holder 21c with respect to the reference angle. Here, $\theta$ represents an angle formed in the X direction with respect to the vertical direction, and $\eta$ represents an angle formed in the Y direction with respect to the vertical direction.

The position change drive 23 and the angle change drive 24 each include a motor (a stepping motor, for example), and are disposed inside or in the vicinity of the linear movement mechanism 21a, for example. The position change drive 23 can change the arrangement positions (X, Y, Z) of the support rod 21b and the X-ray source holder 21c based on a command from the suspension-side controller 25. Furthermore, the angle change drive 24 changes the X-ray irradiation center angle ($\theta$, $\eta$) of the X-ray source 11a, which is the inclination angle of the X-ray source holder 21c, based on a command from the suspension-side controller 25.

The position change drive 23 includes a position detector including an encoder, for example, and the angle change drive 24 includes an angle detector including an encoder, for example. Information about the arrangement position (X, Y, Z) of the X-ray source 11a is transmitted to the suspension-side controller 25 by the position change drive 23, and information about the X-ray irradiation center angle ($\theta$, $\eta$) of the X-ray source 11a is transmitted to the suspension-side controller 25 by the angle change drive 24. In the following description, assuming that the coordinate of the X-ray source 11a in the Y direction is not changed from 0 and the coordinate of the X-ray source 11a in the Z direction is not changed from D1 for ease of explanation, the arrangement position (L, 0, D1) of the X-ray source 11a is described as an offset distance L when a reference position O is set to (0, 0, 0). Furthermore, assuming that the inclination angle $\eta$ of the X-ray source 11a in the Y direction is not changed from 0, the X-ray irradiation center angle ($\theta$, 0) is described as the X-ray irradiation center angle $\theta$ when the reference angle is set to (0, 0). The offset distance L and the X-ray irradiation center angle $\theta$ are examples of a "relative position of the imager" in the claims.

As shown in FIG. 8, when the plurality of X-ray images E are captured, the suspension 2 moves the X-ray source 11a along the X direction to change the offset distance L and changes the inclination direction of the X-ray source 11a each time one X-ray image E is captured so as to change the X-ray irradiation center angle $\theta$. For example, when the X-ray image E1 (No. 1) is captured, the X-ray source 11a is disposed at a position at which the offset distance is 0, and the offset angle is set to 0. Incidentally, the operation of disposing the X-ray source 11a at the position at which an offset distance L0 is 0 and the operation of setting the offset angle to 0 may be automatically performed by the suspension 2 or may be manually performed by the operator. When an X-ray image E2 (No. 2) is captured, the X-ray source 11a is moved to a position at which the offset distance is Lm by the suspension 2. Thereafter, the X-ray source 11a is moved to a position corresponding to each target offset distance Ln by the suspension 2, and the angle of the X-ray source 11a is changed to each target offset angle $\theta n$. At each position, X-ray imaging is performed by the imager 11.

In the present embodiment, the suspension 2 changes the relative position between the X-ray source 11a and the FPD 11b and the relative angle between the X-ray source 11a and the FPD 11b in a state in which a relative position and a relative angle between the FPD 11b and the phantom 4 are kept constant. That is, in a state in which the phantom 4 is placed in the vicinity of the region of interest ROI (see FIG. 2) on the FPD 11b, the suspension 2 moves only the X-ray source 11a without moving the FPD 11b.

(Structures of Image Generation Device and Phantom)

As shown in FIG. 1, the image generation device 3 generates the tomographic image Et parallel to the movement direction of the imager 11 based on the plurality of X-ray images E obtained by X-ray imaging of the imager 11 and position information of the position reference portions 41 and 42 that appear in the plurality of X-ray images E. Specifically, the image generation device 3 includes an image generation controller 31, a tomographic image display 32, a tomographic image storage 33, and a communicator 34.

The image generation controller 31 includes a processor such as a CPU (Central Processing Unit), a GPU (Graphics Processing Unit), and an FPGA (Field-Programmable Gate Array) for image processing. The image generation controller 31 controls the operation of each portion of the image generation device 3.

Furthermore, the image generation controller 31 acquires the plurality of X-ray images E captured by the imager 11 from the generator 1, reconstructs the plurality of acquired X-ray images E, and generates the tomographic image Et a reconstructed image. As the reconstruction processing of the image generation controller 31, a T-SMART method (Tomosynthesis Shimadzu Artifact Reduction Technology), which is a method that applies successive approximation, can be used, for example.

The tomographic image display 32 displays the generated tomographic image Et. In addition, the tomographic image storage 33 includes a nonvolatile memory (a hard disk, for example), and stores the generated tomographic image Et. The communicator 34 can transmit the tomographic image Et to an external network (not shown) or an external device.

The phantom 4 includes the position reference portions 41 and 42, and is disposed at a position at which the position reference portions 41 and 42 appear together with the region of interest ROI of the subject T in the plurality of X-ray images E. Furthermore, the relative position of the phantom 4 to the FPD 11b is fixed. Portions other than the position reference portions 41 and 42 of the phantom 4 are made of resin, for example. The position reference portions 41 and 42 each include an X-ray absorber that absorbs X-rays. Thus, the image generation controller 31 can detect the positions of the position reference portions 41 and 42. In addition, the position reference portions 41 and 42 are provided at positions spaced apart from each other inside or on a surface of the phantom 4. For example, the position reference portions 41 and 42 are made of heavy metals. The heavy metals include gold, lead, tungsten, etc., for example.

The image generation controller 31 acquires the reference position information F, which is the position information (coordinate position information) of the position reference portions 41 and 42 in each X-ray image E, and performs reconstruction processing based on the acquired reference position information F. For example, at the time of the reconstruction processing, the image generation controller 31 performs correction processing (position correction, image unevenness correction, etc.) and processing for not including an inappropriate X-ray image E of the plurality of X-ray images E in images that constitute the tomographic image Et, based on the reference position information F.
(Structure of Suspension-Side Controller)

The suspension-side controller 25 includes a processor such as a CPU and an FPGA. As shown in FIG. 9, in the present embodiment, the suspension-side controller 25 includes the target determiner 25a and the drive controller 25b. Here, the target determiner 25a and the drive controller 25b may be separate pieces of hardware or a functional block in the suspension-side controller 25 as one piece of hardware.
<Structure of Target Determiner>

The target determiner 25a determines the target offset distance Ln of the imager 11 and the target offset angle θn of the imager 11 based on the imaging content information G for generating the tomographic image Et in order to capture the X-ray image. Note that "determining the target offset distance Ln and the target offset angle θn" may indicate calculating the target offset distance Ln and the target offset angle θn by performing calculations based on the following mathematical formulas, for example, or acquiring the target offset distance Ln and the target offset angle θn by referring to a table or the like in which the angle information C2 and the number information C3 are associated in advance with the target offset distance Ln and the target offset angle θn. The target offset distance Ln is an example of a "target position" or an "X-ray source target position" in the claims. The target offset angle θn is an example of a "target angle" or an "X-ray source target angle" in the claims.

In the present embodiment, the target determiner 25a determines the target offset distance Ln of the X-ray source 11a with respect to the FPD 11b and the target offset angle θn of the X-ray source 11a with respect to the FPD 11b based on the imaging content information G.

Specifically, the suspension-side controller 25 (target determiner 25a) acquires the imaging content information G (comment information C) from the generator-side controller 13 of the generator 1. The target determiner 25a determines the target offset distance Ln and the target offset angle θn corresponding to each of the plurality of X-ray images E to be captured based on the angle information C2 and the number information C3 contained in the imaging content information G (comment information C).

More specifically, first, the target determiner 25a determines whether or not the tomosynthesis command information C1 is contained in the imaging content information G (in the comment information C). Then, the target determiner 25a determines the target offset distance Ln and the target offset angle θn corresponding to each of the plurality of X-ray images E to be captured based on the angle information C2 and the number information C3 when the tomosynthesis command information C1 is contained in the imaging content information G (in the comment information C).

As shown in FIG. 8, the target determiner 25a acquires imager distance information J1, which is information indicating a distance D1 (SID: source image receptor distance) from the FPD 11b to the X-ray source 11a when the first (No. 1) X-ray image E1 is captured, and dimension information J2, which is information indicating the dimension (width V: see FIG. 7) of a region of the FPD 11b irradiated with X-rays from the X-ray source 11a, and determines the target offset distance Ln and the target offset angle θn based on the imager distance information J1, the dimension information J2, and the imaging content information G.

Here, the angle information C2 contains information about the maximum imaging angle φm with respect to the reference angle of 0 degrees (a direction along the Z direction). The target determiner 25a acquires (calculates) the maximum offset distance Lm based on the distance D1 and the angle information C2 (imaging angle φm). Specifically, the target determiner 25a acquires the maximum target offset distance Lm based on the following formula (1). Note that the imaging angle φm indicates an angle formed between a line segment that connects the reference position O and the X-ray source 11a and the Z direction (Z-axis) at the reference position O, and is distinguished from the aforementioned X-ray irradiation center angle θ.

[Mathematical Formula 1]

$$Lm = D1 \times \tan(\varphi m) \quad (1)$$

The target determiner 25a acquires the target offset distance Ln corresponding to the X-ray image E to be n-th captured based on the number information C3 (information about the total number N of images to be captured). Specifically, as shown in FIG. 10, the target determiner 25a acquires an interval between the target offset distances Ln as $(Lm \times 2)/(N-1)$. Furthermore, the target determiner 25a sets a target offset distance L1 corresponding to the first X-ray image E1 to 0 and sets a target offset distance L2 corresponding to the second X-ray image E2 as Lm. Furthermore, the target determiner 25a sets a target offset distance L3 corresponding to a third X-ray image E3 as $Lm-\{(Lm \times 2)/(N-1)\}$. In other words, the suspension 2 moves the X-ray source 11a in an X1 direction by the offset distance Lm at the time of X-ray imaging (at the time of tomosynthesis imaging), and then moves the X-ray source 11a in an X2 direction by a distance twice the offset distance Lm.

For example, when the total number N of images to be captured is 3, the target offset distances L1, L2, and L3 are 0, Lm, and −Lm. When the total number N of images to be captured is 5, the target offset distances L1, L2, L3, L4, and L5 are 0, Lm, Lm/2, −Lm/2, and −Lm. When the total number N of images to be captured is 7, the target offset distances L1, L2, L3, L4, L5, L6, and L7 are 0, Lm, 2×Lm/3, Lm/3, −Lm/3, −2×Lm/3, and −Lm.

Here, as shown in FIG. 7, the angle of a line segment that connects the X-ray source 11a and an end 111b of the FPD 11b on the X1 direction side with respect to the reference angle of 0 degrees (Z direction) is defined as an, and the angle of a line segment that connects the X-ray source 11a and an end 211b of the FPD 11b on the X2 direction side with respect to the reference angle of 0 degrees (Z direction)

is defined as βn, the target offset angle θn can be expressed using the following formula (2).

[Mathematical Formula 2]

$$\theta_n = \tfrac{1}{2}(\alpha_n + \beta_n) \qquad (2)$$

Here, the angles αn and βn have the relationships of formulas (3) and (4), respectively, using the target offset distance Ln, the width V (irradiation field size), and the distance D1 (SID).

[Mathematical Formula 3]

$$\alpha_n = \tan^{-1}\left(\frac{2Ln - V}{2D1}\right) \qquad (3)$$

$$\beta_n = \tan^{-1}\left(\frac{2Ln + V}{2D1}\right) \qquad (4)$$

Therefore, the target offset angle θn has the relationship of the following formula (5) with the target offset distance Ln, the width V, and the distance D1. The target determiner 25a determines the target offset angle θn shown in the above formula (5) based on the target offset distance Ln, the width V, and the distance D1.

[Mathematical Formula 4]

$$\theta_n = \frac{1}{2}(\alpha_n + \beta_n) = \frac{1}{2}\tan^{-1}\left(\frac{8LnD1}{4D1^2 - 4Ln^2 + V^2}\right) \qquad (5)$$

<Structure of Drive Controller>

As shown in FIG. 7, in the present embodiment, the drive controller 25b controls the position change drive 23 and the angle change drive 24 to be driven such that the relative position (offset distance L) of the imager 11 corresponds to the target offset distance Ln and the relative angle (X-ray irradiation center angle θ) of the imager 11 corresponds to the target offset angle θn of the imager 11.

Here, the relative position of the imager 11 indicates the offset distance L of the X-ray source 11a with respect to the FPD 11b in the X direction. That is, the offset distance L corresponds to an X coordinate when the center point of the FPD 11b is set as the reference position O. The relative angle of the imager 11 indicates the X-ray irradiation center angle θ of the X-ray source 11a with respect to the FPD 11b. That is, the relative angle corresponds to a θ coordinate when the center point of the FPD 11b is set as the reference position O. Furthermore, "the relative position of the imager 11 corresponds to the target offset distance Ln" means that the offset distance L of the X-ray source 11a coincides with the target offset distance Ln, for example. Furthermore, "the relative angle of the imager 11 corresponds to the target offset angle θn" means that the X-ray irradiation center angle θ coincides with the target offset angle θn, for example.

Specifically, in the present embodiment, the drive controller 25b acquires the imaging step information C4 (information indicating n) from the generator-side controller 13. That is, the suspension-side controller 25 including the drive controller 25b acquires the imaging step information C4 contained in either the comment information C or information about the imaging conditions from the generator-side controller 13.

Then, the drive controller 25b controls the position change drive 23 and the angle change drive 24 to be driven such that the relative position of the imager 11 corresponds to the target offset distance Ln corresponding to the acquired imaging step information C4 and the relative angle of the imager 11 corresponds to the target offset angle θn corresponding to the acquired imaging step information C4.

The drive controller 25b acquires the drive start signal S1 from the generator 1, and starts driving of the position change drive 23 and the angle change drive 24 in accordance with the acquired drive start signal S1. That is, when the operator operates the movement operation unit 17 of the generator 1, the position change drive 23 and the angle change drive 24 are driven such that the X-ray source 11a is moved to a position at which the offset distance L of the X-ray source 11a becomes the target offset distance Ln and the X-ray irradiation center angle θ becomes the target offset angle θn. Then, when the offset distance L coincides with the target offset distance Ln and the X-ray irradiation center angle θ coincides with the target offset angle θn, the drive controller 25b transmits the movement completion signal S2 to the generator-side controller 13.

[X-Ray Image Capturing Method]

Figure 11:
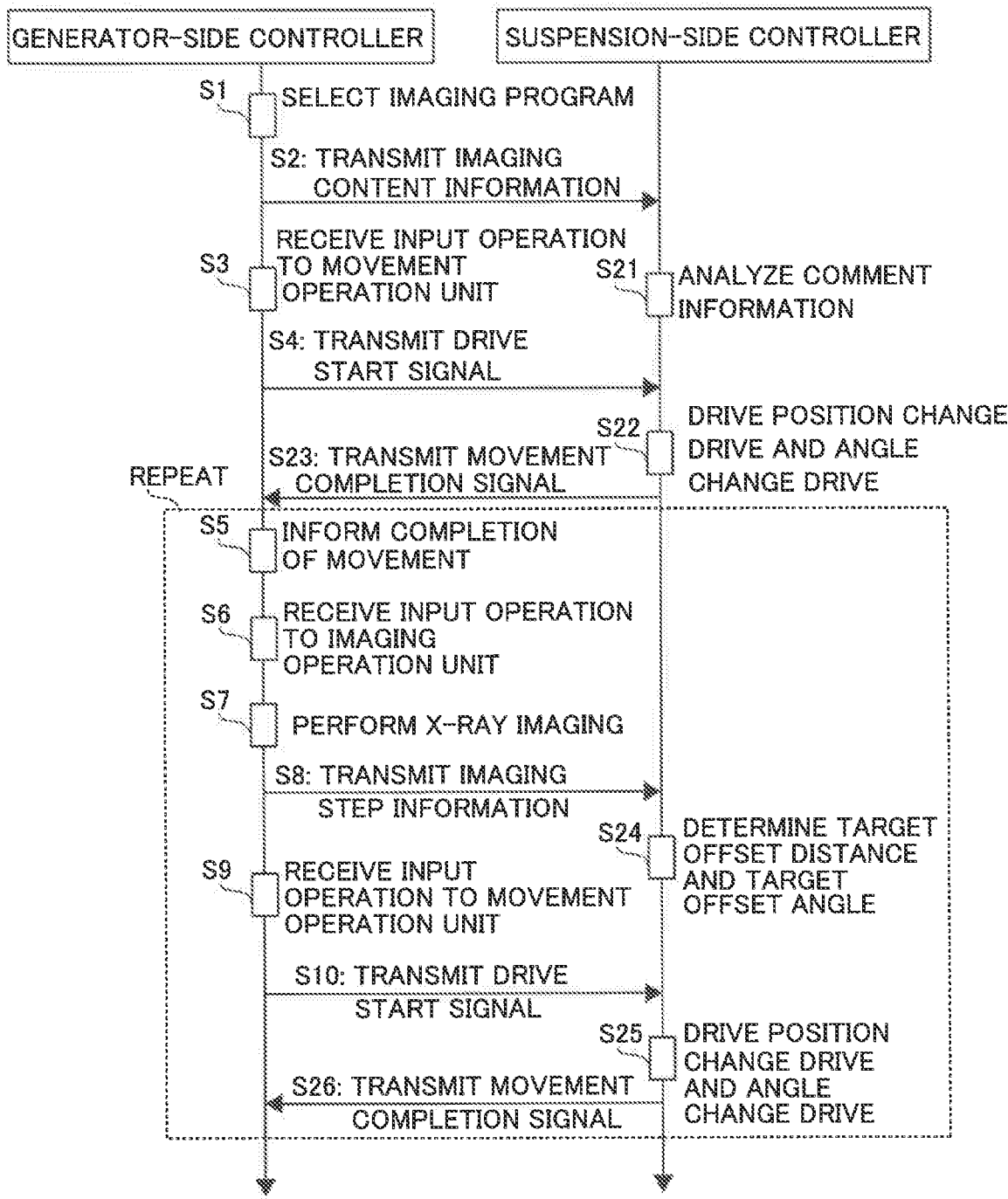
FIG. 11 is a sequence diagram illustrating signal exchange between a generator-side controller and the suspension-side controller according to the embodiment.

An X-ray image capturing method performed by the X-ray image capturing apparatus 100 according to the present embodiment is now described with reference to FIG. 11. As to this X-ray image capturing method, particularly, signal exchange between the generator-side controller 13 and the suspension-side controller 25, and control processing performed by the generator-side controller 13 and the suspension-side controller 25 are described. FIG. 11 shows a sequence diagram showing the signal (data) exchange between the generator-side controller 13 and the suspension-side controller 25 and the control processing performed by the generator-side controller 13 and the suspension-side controller 25.

In step S1, the generator-side controller 13 performs imaging program selection processing. Specifically, the imaging step display screen P1 (see FIG. 3) corresponding to the selection display 58 touched on the imaging program display screen P2 (see FIG. 6) is displayed on the touch panel 14.

In step S2, the imaging content information G is transmitted from the generator-side controller 13 to the suspension-side controller 25. Then, the imaging content information G is acquired by the suspension-side controller 25.

In step S21, analysis processing of the comment information C is performed by the suspension-side controller 25. That is, when the tomosynthesis command information C1, the angle information C2, and the number information C3 (see FIG. 4) are contained in the imaging content information G (comment information C), the suspension-side controller 25 performs an operation in step S24, assuming that the tomosynthesis image is to be captured. When the tomosynthesis command information C1, the angle information C2, and the number information C3 are not contained, the suspension-side controller 25 does not perform the operation in step S24.

In step S3, the generator-side controller 13 receives the input operation through the movement operation unit 17. Then, in step S4, when the input operation through the movement operation unit 17 is acquired by the generator-side controller 13, the drive start signal S1 is transmitted from the generator-side controller 13 to the suspension-side controller 25.

In step S22, in response to acquiring the drive start signal S1, the drive controller 25b of the suspension-side controller 25 starts driving of the position change drive 23 and the angle change drive 24. For example, the position change drive 23 and the angle change drive 24 are driven such that the X-ray source 11a is disposed at the position at which the offset distance of the X-ray source 11a is 0 (a position directly above the reference position O, for example) and the X-ray irradiation center angle θ of the X-ray source 11a is 0.

In step S23, based on the fact that the X-ray source 11a has been disposed at the position at which the offset distance is 0, and the X-ray irradiation center angle θ has become 0, the movement completion signal S2 is transmitted from the suspension-side controller 25 to the generator-side controller 13.

In step S5, the generator-side controller 13 controls the notifier 18 to inform that the movement and angle change of the imager 11 (X-ray source 11a) have been completed. For example, sound is output from the notifier 18, or a lamp as the notifier 18 is turned on or blinked.

In step S6, the generator-side controller 13 receives the input operation through the imaging operation unit 16. Then, in step S7, when the input operation through the imaging operation unit 16 is acquired by the generator-side controller 13, the FPD 11b is irradiated with X-rays from the X-ray source 11a. Then, the detection signal is transmitted from the FPD 11b to the image generation device 3.

In step S8, the imaging step information C4 (comment information C) is transmitted from the generator-side controller 13 to the suspension-side controller 25. Specifically, the generator-side controller 13 notifies the suspension-side controller 25 of which one of the plurality of X-ray images E the X-ray image E to be next captured by X-ray imaging corresponds to (current step).

Here, in the present embodiment, in step S24, the target determiner 25a of the suspension-side controller 25 determines the target offset distance Ln of the imager 11 and the target offset angle θn of the imager 11 based on the imaging content information G for generating the tomographic image Et in order to capture the X-ray image E.

In step S9 and step S10, processing similar to step S3 and processing similar to step S4 are executed, respectively. Furthermore, in step S25 and step S26, processing similar to step S22 and processing similar to step S23 are executed, respectively. The processing in step S5 to step S10 and the processing in step S24 to S26 are repeated until all the X-ray images E in the imaging programs are captured. Thereafter, the image generation device 3 generates the tomographic image Et parallel to the movement direction (X direction) of the imager 11, which is the direction in which the imager 11 is moved by the suspension 2, based on the plurality of X-ray images E and the reference position information F, which is the position information of the position reference portions 41 and 42 that appear in the plurality of X-ray images E.

Advantageous Effects of Present Embodiment

According to the present embodiment, the following advantageous effects are achieved.

According to the present embodiment, as described above, the X-ray image capturing apparatus 100 includes the target determiner 25a that determines the target offset distance Ln and the target offset angle θn based on the imaging content information G for generating the tomographic image Et in order to capture the X-ray image E, and the drive controller 25b that controls the position change drive 23 and the angle change drive 24 to be driven such that the offset distance L of the imager 11 corresponds to the target offset distance Ln and the X-ray irradiation center angle θ of the imager 11 corresponds to the target offset angle θn. Accordingly, a plurality of target offset distances Ln and a plurality of target offset angles θn can be determined (calculated, for example) based on the imaging content information G. Consequently, there is no need to prepare (register and store) the imaging content information G for each X-ray image E, and thus an increase in the number of pieces of imaging content information G can be significantly reduced or prevented. In addition, the drive controller 25b can automatically drive the position change drive 23 and the angle change drive 24 (move the imager 11) such that the offset distance L of the imager 11 corresponds to the target offset distance Ln and the X-ray irradiation center angle θ of the imager 11 corresponds to the target offset angle θn, and thus the work burden on the operator can be reduced as compared with the case in which the imager 11 is manually moved by the operator. Consequently, even when the tomographic image Et parallel to the movement direction of the imager 11 is generated based on the reference position information F, an increase in the number of pieces of imaging content information G that needs to be stored in advance can be significantly reduced or prevented while the work burden on the operator is reduced.

According to the present embodiment, as described above, the imaging content information G contains the angle information C2 of the imager 11 and the number information C3 of the X-ray images E to be captured by X-ray imaging, and the target determiner 25a determines the target offset distance Ln and the target offset angle θn corresponding to each of the plurality of X-ray images E to be captured based on the angle information C2 of the imager 11 and the number information C3 of the X-ray images E. Accordingly, the target determiner 25a can acquire the number of X-ray images E (the total number N of images to be captured) required to generate (reconstruct) the tomosynthesis image and the angle information C2 of the imager 11 when the X-ray images E are captured by X-ray imaging, and thus the target offset distance Ln and the target offset angle θn corresponding to each X-ray image E required to generate (reconstruct) the tomosynthesis image can be determined (calculated) based on one piece of imaging content information G.

According to the present embodiment, as described above, the X-ray image capturing apparatus 100 includes the generator 1 including the generator-side controller 13 that controls the operation of the X-ray source 11a. Furthermore, the suspension 2 includes the suspension-side controller 25 including the target determiner 25a, and the suspension-side controller 25 acquires the imaging content information G from the generator-side controller 13 of the generator 1. Accordingly, even when the imaging content information G is stored (or set) in the generator 1 different from the suspension 2, the suspension-side controller 25 including the target determiner 25a can acquire (receive, for example) the imaging content information G from the generator 1.

According to the present embodiment, as described above, the imaging content information G is the comment information C input via the input operation by the operator, and the suspension-side controller 25 acquires the comment information C from the generator-side controller 13. Accordingly, the suspension-side controller 25 can acquire the imaging content information G as the comment information C from the generator-side controller 13, and thus the operator inputs the imaging content information G into the comment information C without using a dedicated generator-side controller 13 (without changing the software of the generator-side controller 13) such that the target determiner 25*a* of the suspension 2 can acquire the imaging content information G.

According to the present embodiment, as described above, the generator 1 includes the touch panel 14 that receives an input operation for the comment information C from the operator and that displays the comment information C. Accordingly, the input operation by the operator can be received through the touch panel 14 while the operator visually recognizes the contents of the comment information C on the touch panel 14, and thus the convenience of the input operation by the operator can be improved.

According to the present embodiment, as described above, the imaging content information G contains the imaging step information C4 indicating which one of the plurality of X-ray images E the X-ray image E to be next captured by X-ray imaging corresponds to. Furthermore, the drive controller 25*b* acquires the imaging step information C4 from the generator-side controller 13, and controls the position change drive 23 and the angle change drive 24 to be driven such that the offset distance L of the imager 11 corresponds to the target offset distance Ln corresponding to the acquired imaging step information C4 and the X-ray irradiation center angle θ of the imager 11 corresponds to the target offset angle θn corresponding to the acquired imaging step information C4. Accordingly, even when the plurality of target offset distances Ln and the plurality of target offset angles θn are determined (calculated), the imager 11 can be appropriately moved (changed in angle) to the target offset distance Ln and the target offset angle θn corresponding to the X-ray image E to be next captured by X-ray imaging based on the imaging step information C4.

According to the present embodiment, as described above, the generator 1 includes the movement operation unit 17 that receives an input operation indicating that driving of the position change drive 23 and the angle change drive 24 is to be started from the operator, and the drive controller 25*b* starts driving of the position change drive 23 and the angle change drive 24 such that the offset distance L of the imager 11 corresponds to the target offset distance Ln and the X-ray irradiation center angle θ of the imager 11 corresponds to the target offset angle θn in accordance with the input operation indicating that driving of the position change drive 23 and the angle change drive 24 is to be started. Accordingly, the operator can start driving of the position change drive 23 and the angle change drive 24 through the movement operation unit 17 at the intended time (timing). Consequently, when the X-ray image capturing apparatus 100 is used as a medical X-ray image capturing apparatus, the position change drive 23 and the angle change drive 24 can be driven (the imager 11 can be moved) at the appropriate timing according to the state (such as the posture) of the subject.

According to the present embodiment, as described above, the target determiner 25*a* acquires the information about the distance D1, which is the information indicating the distance from the FPD 11*b* to the X-ray source 11*a* when the X-ray image E is captured as the first X-ray image E by X-ray imaging, and the information about the width V, which is the information indicating the dimension of the region of the FPD 11*b* irradiated with X-rays from the X-ray source 11*a*, and determines the target offset distance Ln and the target offset angle θn based on the information about the distance D1, the information about the width V, and the imaging content information G. Accordingly, the target offset distance Ln and the target offset angle θn can be easily determined (calculated) from the information about the distance D1 (SID) and the information about the width V (irradiation field size).

According to the present embodiment, as described above, the image generation device 3 generates the tomographic image Et based on the plurality of X-ray images E including the first X-ray image E1 and the reference position information F. Accordingly, the first X-ray image E1 captured by X-ray imaging to acquire the information about the distance D1 and the information about the width V can also be used to generate (reconstruct) the tomographic image Et (tomosynthesis image), and thus an increase in the number of times of X-ray imaging can be significantly reduced or prevented. Consequently, an increase in the X-ray irradiation dose and an increase in the number of operation steps related to X-ray imaging can be significantly reduced or prevented.

According to the present embodiment, as described above, the X-ray image capturing apparatus 100 includes the phantom 4 including the position reference portions 41 and 42 and disposed at a position at which the position reference portions 41 and 42 appear together with the region of interest ROI of the subject T in the plurality of X-ray images E. The suspension 2 changes the offset distance L, which is the relative position between the X-ray source 11*a* and the FPD 11*b*, and the X-ray irradiation center angle θ, which is the relative angle between the X-ray source 11*a* and the FPD 11*b*, in a state in which the relative position and the relative angle between the FPD 11*b* and the phantom 4 are kept constant. Furthermore, the target determiner 25*a* determines the target offset distance Ln of the X-ray source 11*a* with respect to the FPD 11*b* as the target offset distance Ln and the target offset angle θn of the X-ray source 11*a* with respect to the FPD 11*b* as the target offset angle θn based on the imaging content information G. Accordingly, changes (shifts) in the relative position and the relative angle between the FPD 11*b* and the phantom 4 can be significantly reduced or prevented, and thus a more accurate tomographic image Et (tomosynthesis image) can be generated. Furthermore, it is not necessary to determine the target position and the target angle of the FPD 11*b* by determining the target offset distance Ln and the target offset angle θn, and thus an increase in the control load on determination processing (calculation processing) performed by the target determiner 25*a* can be significantly reduced or prevented.

Modified Examples

The embodiment disclosed this time must be considered as illustrative in all points and not restrictive. The scope of the present invention is not shown by the above description of the embodiment but by the scope of claims for patent, and all modifications (modified examples) within the meaning and scope equivalent to the scope of claims for patent are further included.

For example, while the X-ray image capturing apparatus is a medical X-ray image capturing apparatus in the aforementioned embodiment, the present invention is not restricted to this. For example, the X-ray image capturing apparatus may alternatively be an industrial X-ray image capturing apparatus used for product inspection, for example.

While the movement unit is a suspension (overhead traveling X-ray tube suspension) in the aforementioned embodiment, the present invention is not restricted to this. For example, the movement unit may alternatively be an arm-shaped movement mechanism.

Figure 12:
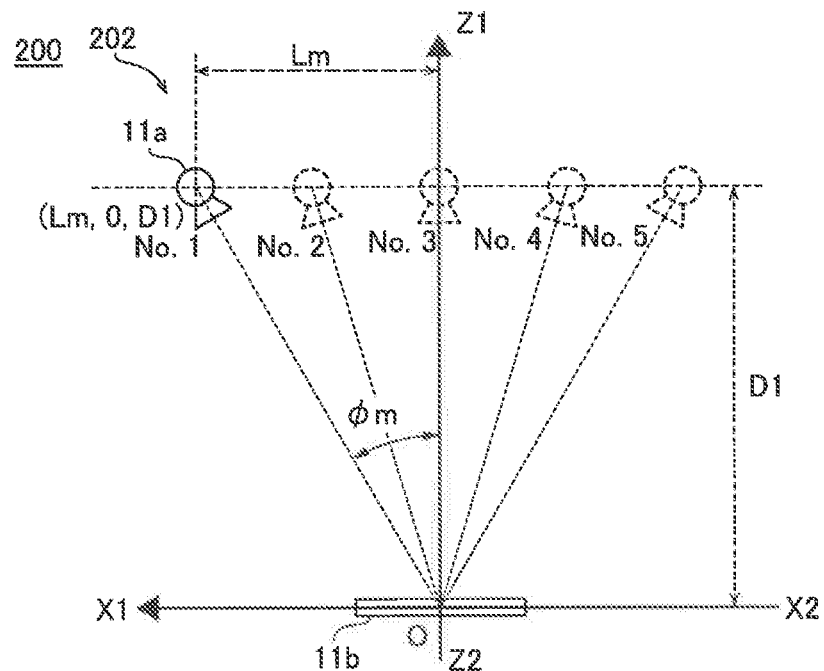
FIG. 12 is a diagram showing the structure of an X-ray image capturing apparatus according to a first modified example of the embodiment.

While in order to capture the first X-ray image, the offset distance of the X-ray source is set to 0, and the X-ray irradiation center angle is set to 0 in the aforementioned embodiment, the present invention is not restricted to this. For example, as in a suspension 202 of an X-ray image capturing apparatus 200 according to a first modified example shown in FIG. 12, in order to capture the first X-ray image, the offset distance of the X-ray source 11a may be set to Lm, and the X-ray irradiation center angle may be set to φm. Note that in order to capture the first X-ray image, the offset distance of the X-ray source is set to 0, and the X-ray irradiation center angle is set to 0 such that positioning is facilitated when the X-ray source is manually disposed at the position at which the first X-ray image is captured.

While in order to capture the plurality of X-ray images, the X-ray source is moved in the X1 direction and then moved in the X2 direction in the aforementioned embodiment, the present invention is not restricted to this. For example, as in the suspension 202 of the X-ray image capturing apparatus 200 according to the first modified example shown in FIG. 12, in order to capture the plurality of X-ray images, the X-ray source 11a may be moved only in the X2 direction from the first (No. 1) to the fifth (No. 5).

Figure 13:
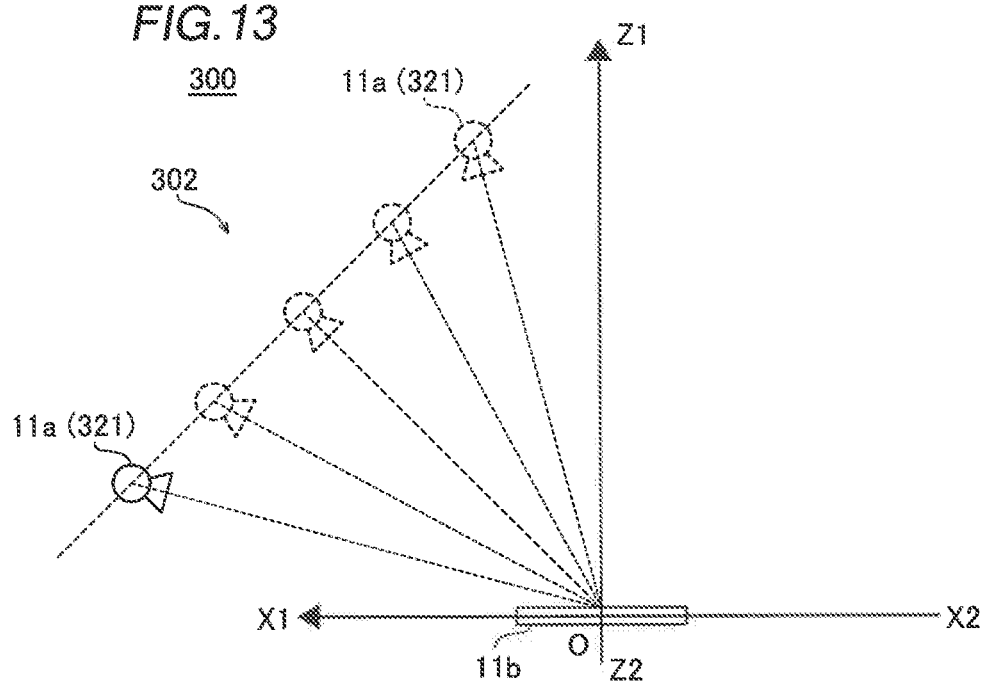
FIG. 13 is a diagram showing the structure of an X-ray image capturing apparatus according to a second modified example of the embodiment.

While the position change mechanism moves the X-ray source (imager) in the X direction in the aforementioned embodiment, the present invention is not restricted to this. For example, as a position change mechanism 321 of a suspension 302 of an X-ray image capturing apparatus 300 according to a second modified example shown in FIG. 13, the position change mechanism may move the X-ray source 11a in a direction that intersects with the X direction.

While the tomosynthesis command information, the angle information, and the number information are contained in the imaging content information in the aforementioned embodiment, the present invention is not restricted to this. For example, the tomosynthesis command information may not be contained in the imaging content information, but the angle information and the number information may be contained in the imaging content information.

While the generator-side controller and the suspension-side controller are separate from each other in the aforementioned embodiment, the present invention is not restricted to this. For example, the generator-side controller and the suspension-side controller may alternatively be a controller including functions of both the generator-side controller and the suspension-side controller.

While the angle information and the number information are the comment information in the aforementioned embodiment, the present invention is not restricted to this. For example, in the X-ray image capturing apparatus, the angle information and the number information may alternatively be transmitted as a control signal other than the comment information from the generator-side controller to the suspension-side controller.

While the touch panel is provided on the generator in the aforementioned embodiment, the present invention is not restricted to this. For example, an operation unit (such as a button and a switch) that receives an input operation and a display including only an image display function may alternatively be separately provided.

While the generator-side controller causes the imaging step information to be contained in the comment information in the aforementioned embodiment, the present invention is not restricted to this. For example, when the imaging step information is transmitted as information other than the comment information from the generator-side controller to the suspension-side controller, the imaging step information may not be contained in the comment information. That is, the second and subsequent comment information may be blank.

While in response to acquiring the drive start signal, the drive controller drives the position change drive and the angle change drive in the aforementioned embodiment, the present invention is not restricted to this. For example, when the X-ray image capturing apparatus is not a medical X-ray image capturing apparatus (when the X-ray image capturing apparatus is an industrial X-ray image capturing apparatus, for example), the drive controller may alternatively drive the position change drive and the angle change drive without acquiring the drive start signal. That is, in the X-ray image capturing apparatus, the movement, angle change, and X-ray irradiation of the X-ray source may be all performed automatically from the first X-ray imaging to the final X-ray imaging.

While the target offset distance is determined by the above formula (1), and the target offset angle is determined by the above formulas (2) to (5) in the aforementioned embodiment, the present invention is not restricted to this. That is, as long as the target offset distance and the target offset angle can be acquired, formulas other than the above formulas (1) to (5) may be used.

While the plurality of X-ray images including the first X-ray image are taken as images that constitute the tomographic image in the aforementioned embodiment, the present invention is not restricted to this. That is, the plurality of X-ray images not including the first X-ray image may alternatively be taken as images that constitute the tomographic image.

While the position of the X-ray source is detected by the position change drive and the angle change drive in the aforementioned embodiment, the present invention is not restricted to this. For example, the suspension-side controller may alternatively acquire information about the position of the X-ray source based on the position of the position reference portion that appears in the X-ray images.

While the total number of images to be captured is set to 3, 5, and 7 in the aforementioned embodiment, the present invention is not restricted to this. That is, the total number of images to be captured may alternatively be other than 3, 5, and 7.

While only the X-ray source of the imager is moved in the aforementioned embodiment, the present invention is not restricted to this. That is, both the X-ray source and the FPD may alternatively be moved, or only the FPD may alternatively be moved.

What is claimed is:

1. An X-ray image capturing apparatus comprising:
   an imager including an X-ray source and a detector that detects X-rays;
   an X-ray generation unit including an X-ray source controller that controls operation of the X-ray source;
   a movement unit including a position change mechanism that changes a relative position and a relative angle between the X-ray source and the detector and a drive that drives the position change mechanism, and that moves the imager;
   an image generator that generates a tomographic image parallel to a movement direction of the imager based on a plurality of X-ray images captured by the imager and reference position information, which is position information of a position reference portion that appears in the plurality of X-ray images;
   a target determiner that determines a target position of the imager and a target angle of the imager based on imaging content information for generating the tomographic image in order to capture each of the X-ray images; and a drive controller that controls the drive to be driven such that the relative position corresponds to the target position of the imager and the relative angle corresponds to the target angle of the imager, wherein the movement unit includes a movement unit-side controller including the target determiner, and the movement unit-side controller acquires the imaging content information from the X-ray source controller of the X-ray generation unit.

2. The X-ray image capturing apparatus according to claim 1, wherein the imaging content information includes angle information of the imager and number information of the X-ray images to be captured by X-ray imaging, and the target determiner determines the target position of the imager and the target angle of the imager corresponding to each of the plurality of X-ray images to be captured based on the angle information of the imager and the number information of the X-ray images.

3. The X-ray image capturing apparatus according to claim 1, wherein the imaging content information is comment information input via an input operation by an operator, and the movement unit-side controller acquires the comment information from the X-ray source controller.

4. The X-ray image capturing apparatus according to claim 3, wherein the X-ray generation unit includes a comment input operation unit that receives the input operation for the comment information from the operator and a display that displays the comment information.

5. The X-ray image capturing apparatus according to claim 1, wherein the imaging content information contains imaging step information indicating which one of the plurality of X-ray images an X-ray image to be next captured by X-ray imaging corresponds to, and the drive controller acquires the imaging step information from the X-ray source controller, and controls the drive to be driven such that the relative position corresponds to the target position of the imager corresponding to the acquired imaging step information and the relative angle corresponds to the target angle of the imager corresponding to the acquired imaging step information.

6. The X-ray image capturing apparatus according to claim 1, wherein the X-ray generation unit includes a drive start operation unit that receives an input operation indicating that driving of the drive is to be started from an operator, and the drive controller starts the driving of the drive such that the relative position corresponds to the target position of the imager and the relative angle corresponds to the target angle of the imager in accordance with the input operation indicating that the driving of the drive is to be started.

7. The X-ray image capturing apparatus according to claim 1, wherein the target determiner acquires imager distance information, which is information indicating a distance from the detector to the X-ray source when a first X-ray image is captured by X-ray imaging, and dimension information, which is information indicating a dimension of a region of the detector irradiated with the X-rays from the X-ray source, and determines the target position of the imager and the target angle of the imager based on the imager distance information, the dimension information, and the imaging content information.

8. The X-ray image capturing apparatus according to claim 7, wherein the image generator generates the tomographic image based on the plurality of X-ray images including the first X-ray image and the reference position information.

9. The X-ray image capturing apparatus according to claim 1, further comprising a phantom including the position reference portion and disposed at a position at which the position reference portion appears together with a region of interest of a subject in the plurality of X-ray images, wherein the movement unit changes the relative position between the X-ray source and the detector and the relative angle between the X-ray source and the detector in a state in which a relative position and a relative angle between the detector and the phantom are kept constant, and the target determiner determines an X-ray source target position of the X-ray source with respect to the detector as the target position of the imager and an X-ray source target angle of the X-ray source with respect to the detector as the target angle of the imager based on the imaging content information.

10. An X-ray image capturing method for generating a tomographic image parallel to a movement direction of an imager, the method comprising:

transmitting, from an X-ray controller to a suspension-side controller, imaging content information;

determining, by the suspension-side controller, a target position of the imager and a target angle of the imager based on the imaging content information for generating the tomographic image in order to capture each of a plurality of X-ray images;

adjusting, by the suspension-side controller and based on the imaging content information, a relative position of the imager to correspond to the target position of the imager and adjusting a relative angle of the imager to correspond to the target angle of the imager;

capturing, along the movement direction, the plurality of X-ray images by the imager; and generating the tomographic image parallel to the movement direction of the imager based on the plurality of X-ray images captured by the imager and reference position information, which is position information of a position reference portion that appears in the plurality of X-ray images.

* * * * *